United States Patent [19]

Mehra

[11] Patent Number: 5,193,536
[45] Date of Patent: Mar. 16, 1993

[54] PACED CARDIOVERSION

[75] Inventor: Rahul Mehra, Stillwater, Minn.

[73] Assignee: Medtronic, Inc., Minneapolis, Minn.

[21] Appl. No.: 630,658

[22] Filed: Dec. 20, 1990

[51] Int. Cl.⁵ ............................................. A61N 1/39
[52] U.S. Cl. ......................... 128/419 D; 128/419 PG
[58] Field of Search ...................... 128/419 D, 419 PG

[56] References Cited

U.S. PATENT DOCUMENTS

| Re. 30,387 | 8/1980 | Denniston, III et al. | 128/419 D |
|---|---|---|---|
| 3,527,228 | 9/1970 | McLaughlin | 128/419 D |
| 3,738,370 | 6/1973 | Charms | 128/419 D |
| 4,363,325 | 12/1982 | Roline et al. | 128/419 PG |
| 4,375,817 | 3/1983 | Engle et al. | 128/419 D |
| 4,384,585 | 5/1983 | Zipes | 128/419 D |
| 4,403,614 | 9/1983 | Engle et al. | 128/419 D |
| 4,408,606 | 10/1983 | Spurrell et al. | 128/419 PG |
| 4,485,818 | 12/1984 | Leckrone et al. | |
| 4,493,325 | 1/1985 | Hartlaub et al. | 128/419 PG |
| 4,503,857 | 3/1985 | Boute et al. | 128/419 PG |
| 4,552,154 | 11/1985 | Hartlaub | 128/702 |
| 4,572,191 | 2/1986 | Mirowski et al. | 128/419 D |
| 4,577,633 | 3/1986 | Berkovits et al. | 128/419 PG |
| 4,787,389 | 11/1988 | Tarjan | 128/419 PG |
| 4,869,252 | 9/1989 | Gilli | 128/419 D |
| 4,895,152 | 1/1990 | Callaghan et al. | 128/419 PG |
| 4,996,984 | 3/1991 | Sweeney | 128/419 D |
| 4,998,974 | 3/1991 | Aker | 128/419 PG |
| 5,002,052 | 3/1991 | Haluska | 128/419 PG |
| 5,074,301 | 12/1991 | Gill | 128/419 D |

Primary Examiner—William E. Kamm
Assistant Examiner—Kennedy J. Schaetzle
Attorney, Agent, or Firm—Reed A. Duthler; Harold R. Patton

[57] ABSTRACT

A cardioverter/pacemaker which provides improved accuracy of the timing of a cardioversion pulse relative to a cardiac depolarization. After detection of a tachyarrhythmia, the device overdrives the tachyarrhythmia with a series of high rate pacing pulses. Delivery of the cardioversion pulse is timed from the last in the series of pacing pulses. In some embodiments, detection of reliable capture by the pacing pulses is a prerequisite to cardioversion synchronized from the pacing pulses.

26 Claims, 6 Drawing Sheets

PACED CARDIOVERSION

BACKGROUND OF THE INVENTION

The present invention relates generally to medical stimulators, and more specifically to implantable cardioverters.

It has been recognized for some time that in delivering a cardioversion pulse, it is desirable to synchronize the pulse to a sensed ventricular tachyarrhythmic depolarization. A device for accomplishing this synchronization is disclosed in U.S. Pat. No. 3,527,228 issued to McLaughlin.

Incorporation of such a synchronization circuit into an implantable defibrillator is disclosed in U.S. Pat. No. 3,738,370 issued to Charms. A later disclosure of a synchronous atrial cardioverter may be found in U.S. Pat. No. 4,572,191, issued to Mirowski et al.

Detection of a tachyarrhythmia episode and thereafter triggering a tachyarrhythmia treatment regimen is also disclosed in U.S. Pat. No. RE 30,387 issued to Denniston et al. Later disclosures of tachyarrhythmia detection methodologies may be found in U.S. Pat. No. 4,403,614 issued to Engle et al., U.S. Pat. No. 4,375,817 issued to Engle et al., U.S. Pat. No. 4,493,325 issued to Hartlaub et al., U.S. Pat. No. 4,384,585 issued to Zipes and U.S. Pat. No. 4,552,154 issued to Hartlaub, all incorporated herein by reference in their entireties.

In addition to delivery of large amplitude defibrillation and/cardioversion pulses, treatment of tachyarrhythmia episodes by means of overdrive pacing has also been extensively researched. One such overdrive pacemaker is disclosed in U.S. Pat. No. 4,577,633, incorporated herein by reference in its entirety. An earlier disclosure of a microprocessor based pacemaker capable of overdrive pacing may be found in U.S. Pat. No. 4,485,818, also incorporated herein by reference in its entirety. In overdrive pacing, the pacemaker senses the rate of the detected tachyarrhythmia and generate pacing pulses at a higher pacing rate, thereafter gradually reducing the pacing rate in an attempt to return the heart rate to a normal range.

SUMMARY OF THE INVENTION

The present invention is directed toward providing an improved implantable synchronous cardioverter/pacemaker. While synchronous cardioversion per se is known to the art, it has been determined that a precise timing relationship between the sensed ventricular depolarization and the delivered cardioversion pulse is desirable in order to provide an implantable cardioverter which operates with maximum efficiency. However, amplifiers of the sort traditionally used with cardiac pacemakers may produce signals indicating the occurrence of depolarizations at different times relative to the sensed depolarizations. Typically, a ventricular contraction is accompanied by an electrical signal or R-wave of at least 50 ms. in duration, and the signal generated by the sense amplifier indicative of occurrence of this depolarization may occur at various points within this 50 ms. period. As such, synchronizing delivery of the cardioversion pulse from the output of a conventional pacemaker sense amplifier provides for some variance in the actual timing relationship between the ventricular depolarization and the associated cardioversion pulse.

The present invention addresses this problem by providing a constant, accurately verifiable timing signal in conjunction with the sensed tachyarrhythmia contraction, from which accurate timing of the cardioversion pulse may be accomplished. Rather than attempting to provide a more sophisticated analysis of the R-wave signal, the invention of the present application provides a fixed timing signal in the form of a cardiac pacing pulse. In response to detection of a tachyarrhythmia, the device according to the present invention generates a series of cardiac pacing pulses at a rate higher than the rate of the detected tachyarrhythmia. The device in some embodiments monitors the heart following delivery of the pacing pulses to determine whether they have successfully captured the heart. The last of a series of overdrive pacing pulses is used as the time reference for delivery of a cardioversion pulse. Thus, the invention provides a simple, yet elegant method of assuring consistency in the timing of cardioversion pulses with relationship to sensed ventricular contractions, for treatment of tachyarrh. The invention is believed to thereby result a reduction in the required to reliably cardiovert the heart and to reduce the chances of accelerating a tachyarrhythmia as a result of a failed cardioversion attempt.

DETAILED DESCRIPTION OF THE PREFERRED EMBODIMENTS

Figure 1:
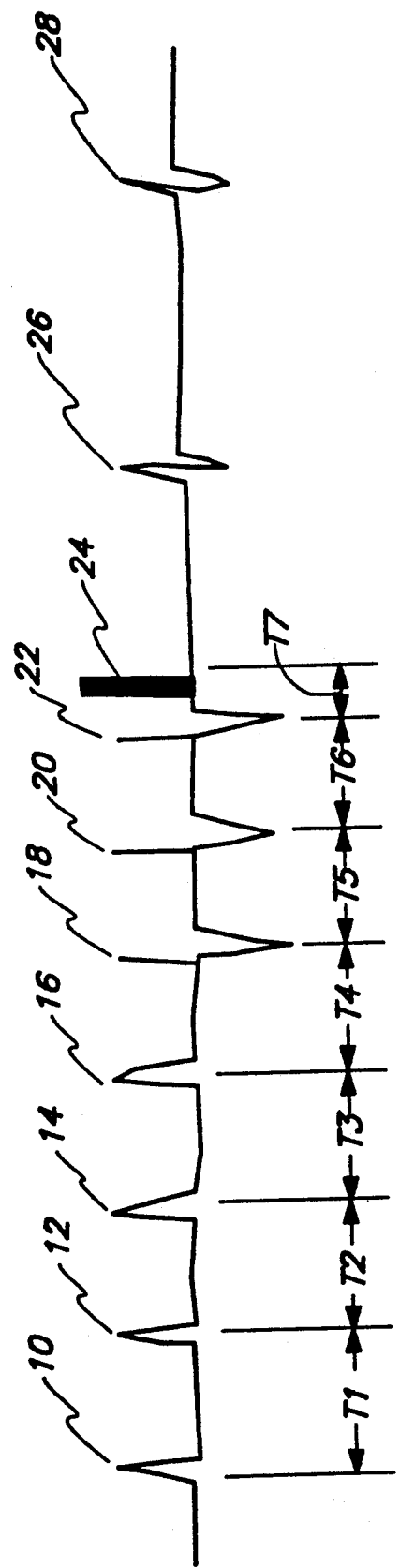
FIG. 1 is a simulated EKG strip illustrating the operation of a device according to the present invention.

FIG. 1 is a simulated EKG strip illustrating the overall operation of the present invention. A series of R-waves 10, 12, 14 and 16 are illustrated, indicative of a ventricular tachyarrhythmia. The cardioverter/pacemaker of the present invention analyzes the cardiac rhythm to determine the presence of a tachyarrhythmia, using any of the various known tachyarrhythmia detection algorithms. The cardioverter/pacemaker also measures the intervals T1, T2, and T3 separating the tachyarrhythmic R-waves.

On determination that a ventricular tachyarrhythmia is present, the rate of the tachyarrhythmia, as manifested by the stored intervals T1, T2 and T3, is used to generate a high rate pacing interval, less than the intervals separating the tachyarrhythmic R-waves. In FIG. 1, this is displayed as time interval T4. On expiration of this interval, a ventricular pacing pulse 18 is generated. In the embodiment illustrated, the cardioverter/pacemaker looks to see whether an R-wave occurs thereafter, indicating that the pacing pulse has captured the heart. However, this capture detection function is not essential to practice the invention. As illustrated in FIG. 1, the pacing pulse was successful in capturing the heart. The cardioverter/pacemaker determines that the pacing pulses are reliably capturing the heart by generating several additional ventricular pacing pulses, 20 and 22, also separated by the high rate pacing interval, illustrated in FIG. 1 as time intervals T5 and T6.

After determining that the pacing pulses are reliably capturing the heart, or after a predetermined number of overdrive pacing pulses if the capture detect function is omitted, the cardioverter/pacemaker generates a cardioversion pulse 24, separated by a cardioversion interval T7 from the last of the pacing pulses 22. Because the pacing pulse 22 and the cardioversion pulse 24 are both generated by the cardioverter, their timed relationship can be controlled with a high degree of accuracy. After an effective cardioversion interval has been determined, it can thus accurately be applied to subsequent tachyarrhythmias.

After delivery of the tachyarrhythmia pulse 24, the heart rhythm is shown as returning to a normal sinus rhythm with ventricular contractions 26 and 28 occurring at intervals T8 and T9 corresponding to normal sinus rhythm. The present invention is believed practicable for use in any implantable cardioverter/pacemaker which has the capability of detecting the occurrence of a ventricular tachyarrhythmia and measuring or deriving the intervals separating the ventricular contractions, during the identified tachyarrhythmia. The cardioverter/pacemaker in which the invention is practiced should also have the ability to determine at least three different timing intervals, corresponding to the high-rate pacing interval, the cardioversion interval, and a lower rate escape interval to allow the device to accomplish normal VVI type demand pacing. In order to derive the high-rate pacing interval an arithmetic logic unit or its equivalent is also required.

Figure 2:
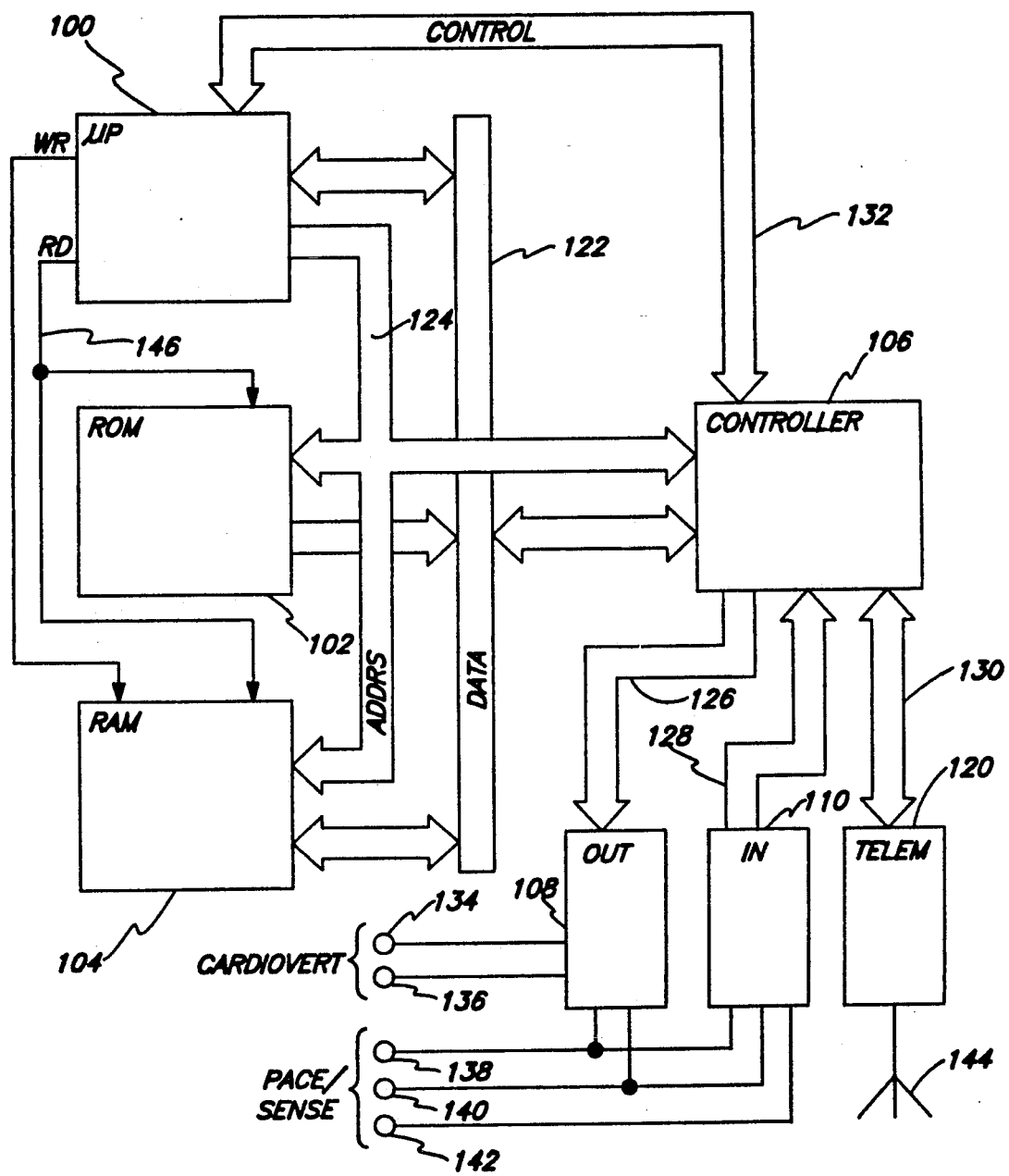
FIG. 2 is a block, functional diagram of a device according to the present invention.

FIG. 2 is a block, functional diagram of an illustrative embodiment of a cardioverter/pacemaker according to the present invention. As illustrated, the device is embodied as a microprocessor based stimulator. However, other digital circuitry embodiments and analog circuitry embodiments are also believed to be within the scope of the invention. FIG. 2 should thus be considered illustrative, rather than limiting with regard to the scope of the invention.

The primary elements of the apparatus illustrated in FIG. 2 are a microprocessor 100, read only memory 102, random access memory 104, a digital controller 106, input and output amplifiers 110 and 108 respectively, and a telemetry/programming unit 120.

Read only memory stores the basic programming for the device, including the primary instruction set defining the computations performed to derive the various timing intervals employed by the cardioverter. Random access memory 104 serves to store variable control parameters, such as programmed pacing rate, programmed cardioversion intervals pulse widths, pulse amplitudes, and so forth which are programmed into the device by the physician. Random access memory 104 also stores derived values, such as the stored time intervals separating tachyarrhythmia pulses and the corresponding high rate pacing interval. Reading from random access memory 104 and read only memory 102 is controlled by RD line 146. Writing to random access memory 104 is controlled by WR line 148. In response to a signal on RD line 146, the contents of the random access memory 104 or read only memory 102 designated by the then present information on address bus 124 are placed on data bus 122. Similarly, in response to a signal on W-R line 148, information on data bus 122 is written into random access memory 104 at the address specified on the address bus 124.

Controller 106 performs all of the basic control and timing functions of the device. Controller 106 includes at least one programmable timing counter, initiated on ventricular contractions, and timing out intervals thereafter. This counter is used to generate the three basic intervals referred to above, including the cardioversion interval (CDINT), the high rate pacing interval (HRINT) and the ventricular inhibited pacing rate (ESC). On time out of these intervals, controller 106 triggers the appropriate output pulse from output stage 108, as discussed below. Following generation of stimulus pulses controller 106 generates corresponding interrupts on control bus 132, waking microprocessor 100 from its sleep state, allowing it to perform any required mathematical calculations. The timing counter in controller 106 also times out a ventricular refractory period, as discussed below. The time intervals which the timing counter in controller 106 counts prior to timeout are controlled via data from RAM 104, applied to the controller 106 via data bus 122.

Controller 106 also generates wake-up interrupts for microprocessor 100 on the occurrence of sensed ventricular contractions. On occurrence of a sensed ventricular contraction, in addition to an interrupt indicating its occurrence placed on control bus 132, the then current value of the timing counter within controller 106 is placed onto data bus 122, for use by microprocessor 100 in determining whether a tachyarrhythmia is present and for determining the intervals separating individual tachyarrhythmia beats.

Controller 106 also includes several event counters for storing counts corresponding to the number of sequential detected tachyarrhythmia beats, the number of high rate pacing pulses delivered and the number of sequential high rate pacing pulses which capture the heart.

Output stage 108 contains a high output pulse generator capable of generating cardioversion pulses of at least 0.1 joules, to be applied to the patient's heart via electrodes 134 and 136, which are typically large surface area electrodes mounted on or in the heart. Other electrode configurations may also be used, including three or more electrodes arranged within and around the heart. Output circuit 108 is also coupled to electrodes 138 and 140, which are employed to accomplish ventricular cardiac pacing. Electrode 138 is typically located on the distal end of an endocardial lead, and is typically placed in the apex of the right ventricle. Electrode 140 is typically an indifferent electrode mounted on or adjacent to the housing of the cardioverter defibrillator. Output circuit 108 is controlled by control bus 126, which allows the controller 106 to determine the time, amplitude and pulse width of the pulse to be delivered and to determine which electrode pair will be employed to deliver the pulse.

Sensing of heart activity, both to determine the rate of a detected tachyarrhythmia and optionally to determine whether or not ventricular pacing pulses have successfully captured the heart is accomplished by input amplifier 110, which is coupled to electrodes 138, 140 and 142. Electrode 142 may be a ring electrode located on an endocardial lead, spaced from the tip electrode 138, or it may be a far field electrode spaced between the heart and the indifferent electrode 140, remote from the heart. Electrodes 138 and 140 are employed to detect normal ventricular contractions. Electrodes 140 and 142 are employed to detect whether or not delivered pacing pulses have captured the heart. A system for accomplishing these functions is disclosed in U.S. Pat. No. 4,895,152 issued to Callaghan et al., issued Jan. 23, 1990 and incorporated herein by reference in its entirety. Signals indicating both the occurrence of natural ventricular contractions to microprocessor 100 via control bus 132 in the form of interrupts, which serve to wake up microprocessor 100, so that it may perform any necessary calculations or updating of values stored in random access memory 104. External control of the implanted cardioverter/defibrillator is accomplished via telemetry/control block 120 which allows communication between the implanted cardioverter/pacemaker and an external programmer. Any conventional programming/telemetry circuitry is believed workable in the context of the present invention. Information entering the cardioverter/pacemaker from the programmer is passed to controller 106 via bus 130. Similarly, information from the cardioverter/pacemaker is provided to the telemetry block 120 via bus 130.

FIGS. 3, 4, 5 and 6 show a functional flow chart illustrating the operation of the device shown in FIG. 2. These flow charts are intended to illustrate the functional operation of the device, and should not be construed as reflective of a specific form of software or hardware necessary to practice the invention. It is believed that the particular form of software will be determined primarily by the microprocessor architecture employed, and that providing software to accomplish the present invention, given the disclosure herein, is well within the abilities of one of skill in the art.

For purposes of understanding the flow chart, a number of terms need to be defined. "T" is the present value of the timing counter in controller 106. This counter is regularly incremented by clock pulses generated in controller 106, and serves the timer for all basic timing intervals. As described in the flow chart, this counter counts up from zero. However, it could as well take the form of a programmable, jam-in down counter, in which zero represents the time out. In such case, the count in the timing counter would have to be subtracted from the number jammed into the counter to determine the actual time interval to be measured. This counter is reset on the delivery of pacing pulses, cardioversion pulses, or on sensing of natural (unpaced) ventricular contractions.

The first interval determined by the timing counter in controller 106 is the refractory period (REF) following a ventricular pacing pulse or a natural sensed ventricular contraction. Typically, on reading a count equal to the refractory period the timing counter will not be reset. Instead, controller 106 will simply detect the expiration of the refractory period and continue counting. During the refractory period, a signal sensed between electrodes 138 and 140 is ineffective to reset the timing counter in controller 106.

The second time interval determined by controller 106 is the VVI escape interval, (ESC), which corresponds to the interval separating adjacent ventricular pacing pulses, in the absence of natural ventricular contractions. Typically, this interval would be about 800 ms. It is anticipated that the value of this interval would be stored in random access memory 104, and would be programmable via telemetry/programming block 120.

The third interval is the high rate pacing interval, (HRINT), which separates adjacent pacing pulses produced after detection of a tachyarrhythmia, as discussed above. The value corresponding to HRINT is calculated by the microprocessor 100, and stored in RAM 104.

The final intervals determined by the counter in controller 106 are the cardioversion intervals, (CINT-1 and CINT-2), which is the interval separating the cardioversion pulse from the immediately preceding pacing pulse of from the immediately preceding ventricular contraction respectively. These intervals are typically stored in RAM 104, and may be altered by external programming via programming/telemetry block 120, or, in some cases, may be altered by the implantable cardioverter/defibrillator itself.

In addition to the intervals determined by the timer in controller 106, the random access memory contains a stored tachyarrhythmia detection interval (TINT), used in the embodiment illustrated herein to determine the presence of a tachyarrhythmia. While the device illustrated herein determines the presence of a tachyarrhythmia by means of detection of sustained high rate, i.e. detection of a series of ventricular contractions occurring at intervals less than the tachyarrhythmia interval, other tachyarrhythmia detection methods known to the prior art may also be practiced beneficially in conjunction with the present invention. Appropriate tachyarrhythmia detection methods are disclosed in the article "Onset and Stability for Ventricular Tachyarrhythmia Detection in an Implantable Pacer-Cardioverter-Defibrillator", by Olson, et al, published in Computers in Cardiology, October, 1986, Pages 167-170, incorporated herein by reference in its entirety, and are also disclosed in the references discussed in the Background section above.

Controller 106 also includes several additional counters which keep track of various counts related to the operation of the device. One counter stores the number of sequential intervals between natural ventricular contractions which are less than TINT. The value corresponding to this count is referred to in the flow chart as TCNT. A second counter stores the number of high rate pacing pulses that have been delivered, following detection of the tachyarrhythmia. The count stored in this counter is referred to as HRCNT. A third counter keeps track of the number of successive high rate pacing pulses that have been successful in capturing the heart. The count stored in this counter is referred to as CCNT. With this basic information, the flow charts may be readily understood.

Figure 3:
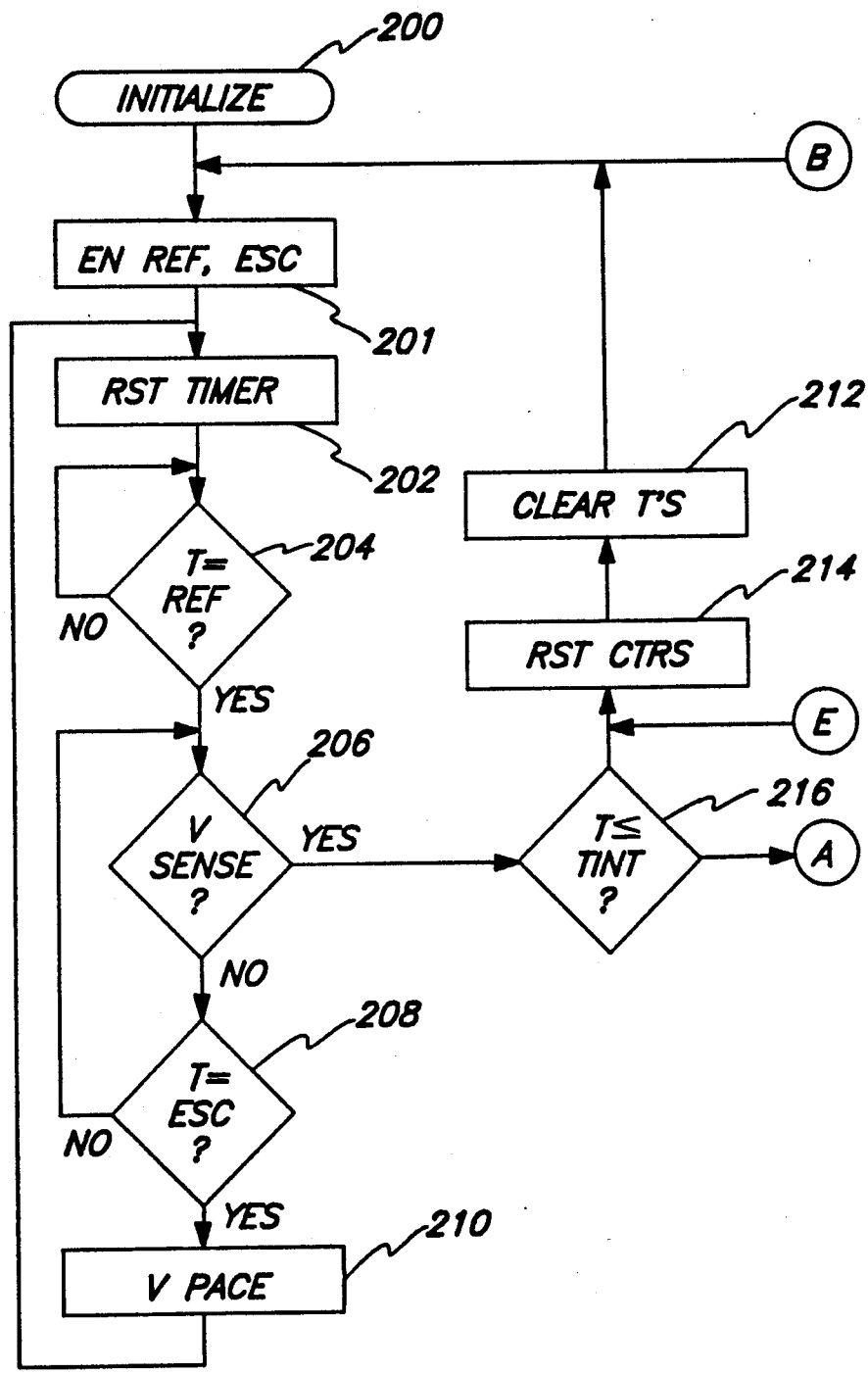
FIGS. 3, 4, 5 and 6 are a functional flow chart, illustrating the operation of the device illustrated in FIG. 2.

FIG. 3 illustrates the main bradycardia pacing routine of the cardioverter/defibrillator of the present invention, and illustrates the exit point to the tachyarrhythmia detection and termination subroutines and the return point from the use of the subroutines. The flow chart begins with an initialization step 200, which may correspond to a power-on reset condition or may correspond to a reprogramming of the parameters of the device via an external programmer. During the initialization step, the TCNT, HRINT and CCNT values are all reset to zero, and the REF, TINT, ESC, and CINT-1 and CINT-2 values are loaded into random access memory 104.

Following initialization, the timing counter is reset to zero at 202. As noted above, in some embodiments this may reflect a loading of a count into the counter, rather than a resetting to zero. Microprocessor 100 enters the sleep mode.

The timing counter in controller 106 continues to count until the count therein equals REF at 204. Following the expiration of the refractory period, controller 106 is responsive to the occurrence of sensed ventricular contractions, as indicated at 206. If no ventricular contraction is sensed prior to the timing counter generating a count equal to ESC at 208, the controller 106 triggers the generation of a ventricular pacing pulse at 210, and is reset to begin timing of the basic bradycardia pacing interval again at 202.

If a ventricular contraction is sensed at 206, an interrupt is generated by controller 106 to wake up microprocessor 100. Microprocessor 100 checks to determine whether the count stored in the timing counter is less than or equal to the value of TINT, stored in random access memory 104. If the value in the timing counter is greater than TINT, microprocessor 100 resets the value of TCNT, stored in the controller 106 to zero via control bus 132 at 214 and clears any intervals corresponding to detected tachyarrhythmic contractions which may be present in random access 104, at 212. If the count in the timing counter in controller 106 is less than or equal to TINT, the microprocessor initiates the tachyarrhythmia detection and treatment functions illustrated in FIGS. 4, 5 and 6.

Figure 4:
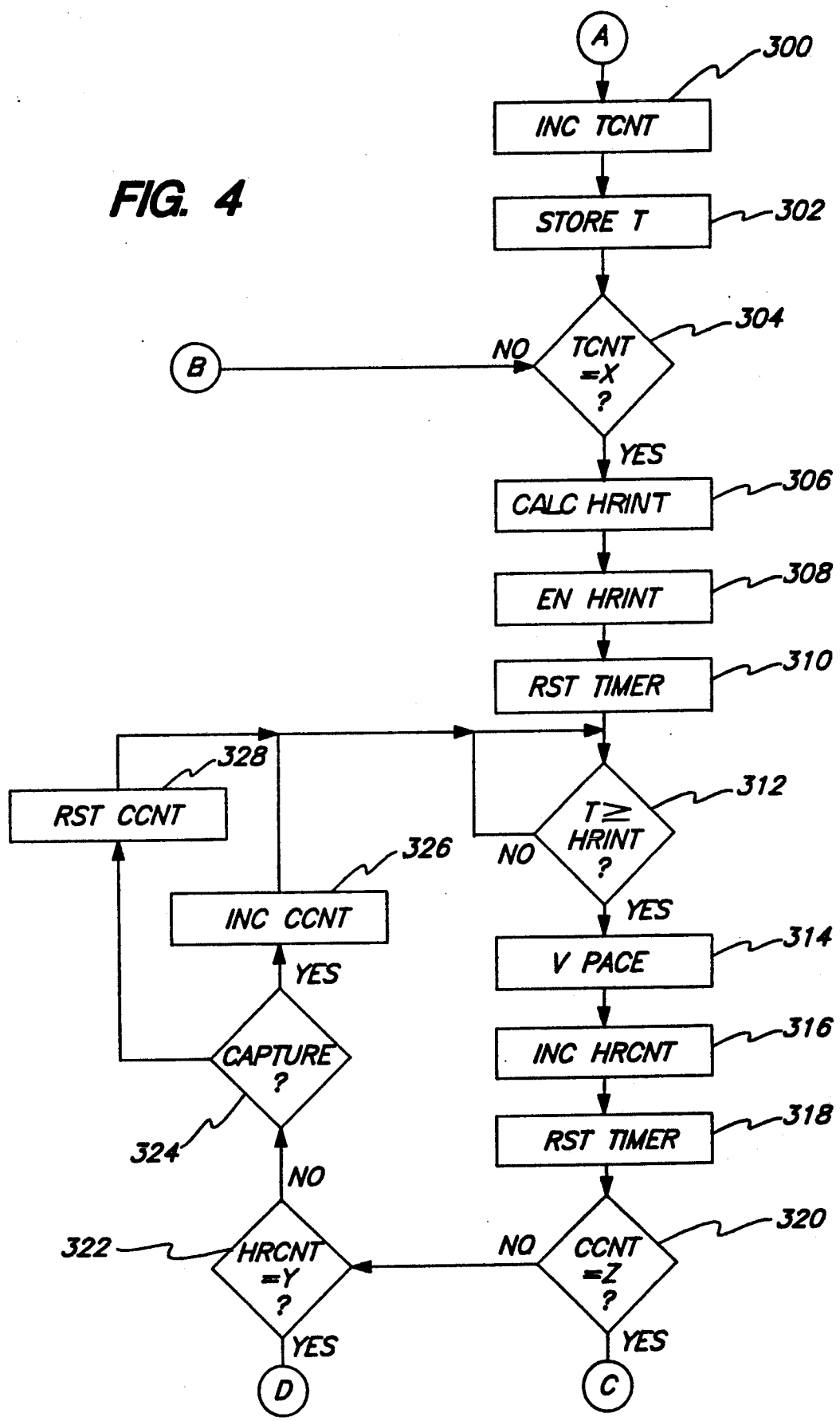

FIG. 4 illustrates the method by which the implantable cardioverter/pacemaker verifies the existence of a tachyarrhythmia and initiates high rate pacing. In response detection of a tachyarrhythmic beat at 216 (FIG. 3), the value of TCNT is incremented at 300, and the duration of the detected tachyarrhythmic interval is stored in the random access memory 104 at 302. The value of TCNT is compared with "X", representing a predetermined number of required sequential intervals meeting the tachyarrhythmic interval criteria. The value of "X" may range widely, but values chosen for X will generally fall in the range of 4 to 32 intervals meeting the tachyarrhythmic interval criteria. If the value of TCNT is less than X, the cardioverter/pacemaker returns to brady pacing via block 201. The microprocessor resets the timing counter at 2 2 and returns to the sleep state while the controller continues to count out the refractory and escape intervals as illustrated in FIG. ?.

In the event that TCNT equals X, the microprocessor calculates a new high rate interval at 306. This accomplished by taking an average of the values of the intervals stored at step 302, and setting HRINT equal to a predetermined percentage of that average. Typically, HRINT will be about 75 to 95 percent of that calculated average.

The microprocessor then enables controller 106 to decode the time-out of the high rate interval at 308 and to trigger ventricular pacing pulses at the expiration thereof, resets the timing counter at 310 and returns to the sleep state while the controller times out the high rate interval. When the high rate interval times out at 312, the controller 106 triggers generation of a pacing pulse at 314, increments the value of HRCNT at 316 and resets the timing counter at 318. The generation of a ventricular pacing pulse at 314 also interrupts the microprocessor 100 and wakes it from its sleep state, after which it compares the stored CCNT value with a predetermined number "Z", indicating the number of sequential high rate pacing pulses which capture the heart, required to initiate delivery of a cardioversion pulse synchronized to a pacing pulse. If this count has been reached at 320, synchronous cardioversion timed off of the pacing pulse is initiated. If not, the microprocessor then checks to determine whether the HRCNT is equal to the maximum number of high rate pacing pulses that will be delivered, designated "Y" at 322. If the maximum number of pacing pulses have been delivered, synchronous cardioversion timed off of the next subsequent natural ventricular contraction will be initiated. If not, the capture detection algorithm is enabled at 324. If capture is detected, the value of CCNT is incremented to 326. If capture is not detected, the value of CCNT is reset to zero at 328. The microprocessor then goes back to sleep while the controller 106 continues to count out the next subsequent high rate pacing interval.

Figure 6:
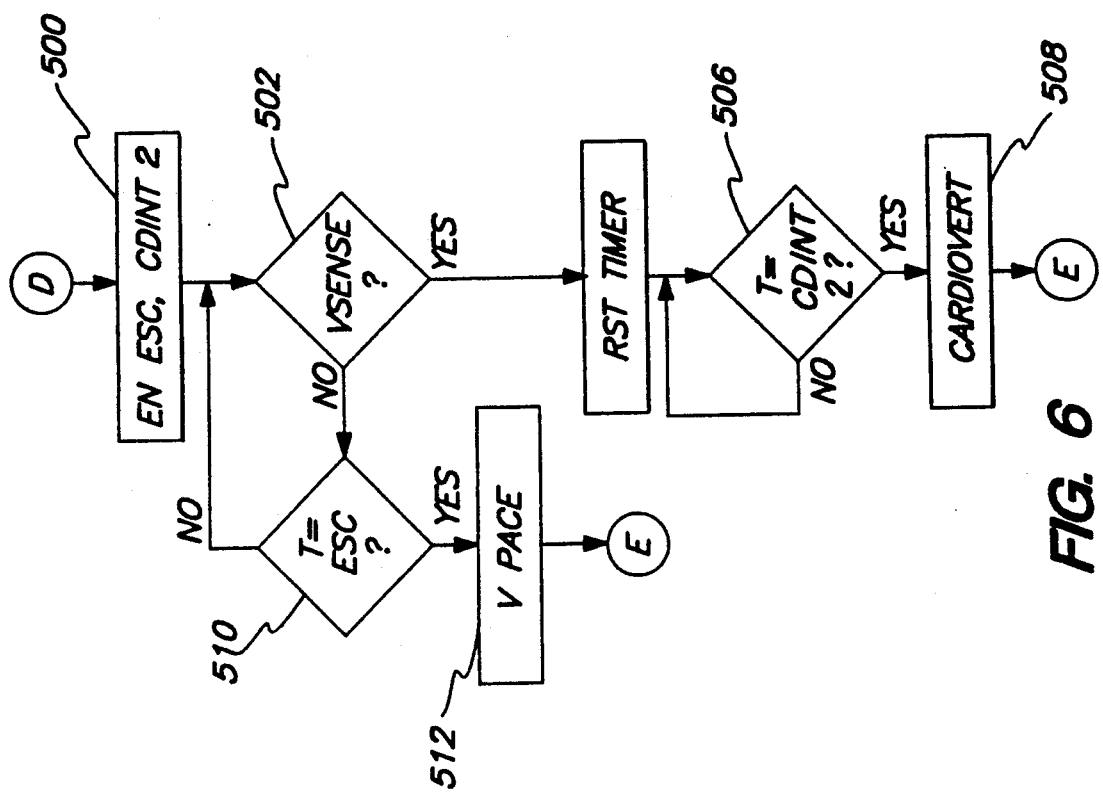

The high rate pacing routine illustrated in FIG. 4 continues until the occurrence of one of two events which trigger delivery of a cardioversion pulse. The first event is the successful capture of the heart by a sequence of Z high rate pacing pulses, not including the most previously delivered pacing pulse. The second event is the generation of the last available high rate pacing pulse, indicated by HRCNT equaling Y. In this event, synchronous cardioversion is enabled following the next sensed ventricular depolarization, as illustrated in FIG. 6. The value of Y must be at least one greater than the value of Z, in order for the routine illustrated to perform properly. Typically, at least two sequential high rate pacing pulses which capture the heart should be required prior to initiating cardioversion in timed synchrony with the next following pacing pulse. The value of Z thus should be 2 or greater. The value of Y therefore would be 3 or greater.

Figure 5:
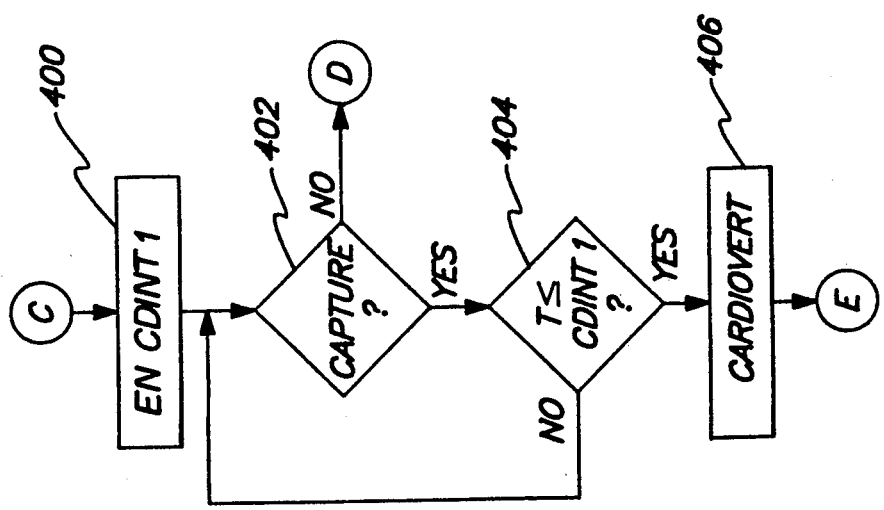

FIG. 5 illustrates a method by which the cardioverter/pacemaker accomplishes cardioversion timed off of the most recent pacing pulse as illustrated in FIG. 1. After determining at 320 that the high rate pacing routine has resulted in Z high rate pacing pulses preceding the most recent delivered pulse capturing the heart, microprocessor 100 enables controller 106 to respond the time out of a cardioversion interval CDINT-1 at 400, and to trigger the output stage 108 to generate a cardioversion pulse at the expiration of CDINT-1. The controller 106, its timer previously reset, thereafter initiates the capture detection routine at 402. If the capture detection routine indicates a failure to capture, cardioversion based on the next subsequent sensed contraction will be attempted, as illustrated in FIG. 6. If the capture detect function indicates that the previous high rate pacing pulse was successful in capturing the heart, the timing counter in controller 106 will continue to time out until reaching a count equal to CDINT-1 at 404, after which a cardioversion pulse will be generated at 406. Following the cardioversion pulse, an interrupt will be generated by controller 106 which wakes microprocessor 100 from its sleep state, allowing it to reset the event counters within the controller at 214 (FIG. 3) and to clear the stored tachyarrhythmia interval values at 212. The microprocessor then re-enables the decoding of the refractory (REF) and escape (ESC) intervals at 201, resets the timer in controller 106 at 202, and returns to the sleep state while the controller 106 functions as a ventricular inhibited pacemaker, as illustrated in FIG. 3.

The step of capture detection at 402 is an optional feature of the device. If the selected value of CDINT-1 is long enough to permit operation of the capture detection routine, the capture detection routine may be employed. If, on the other hand, the duration of CDINT-1 is not sufficient to enable performance of the capture detection function prior to delivery of the cardioversion pulse, this step must of necessity be dispensed with.

In the event that either the maximum number (Y) of high rate pacing pulses have been generated without producing the required number Z of sequential pacing pulses which capture the heart, as indicated at 322, the synchronous cardioversion method illustrated in FIG. 6 is initiated. Similarly, in the event that a failure to capture is detected at 402 (FIG. 5), this synchronous cardioversion method is attempted.

On failure to capture at 402, the microprocessor is awakened from its sleep state, allowing it to re-enable the control logic 106 to detect time out of the escape interval and a second cardioversion pacing interval CDINT-2, which typically will be shorter than the CDINT-1 interval. The microprocessor then returns to its sleep state as controller 106 awaits the occurrence of a sensed ventricular contraction at 502. In the event that no ventricular contraction is sensed prior to time out of the escape interval (ESC) at 510, the controller 106 triggers generation of the pacing pulse at 512, thereafter generating an interrupt signal which awakes the microprocessor 100, allowing it to reset all event counters in the controller at 214, to clear the stored tachyarrhythmia intervals at 212, and then to return to the bradycardia pacing modality as illustrated in FIG. 3. In the event that a ventricular depolarization is sensed at 502, the timing counter is reset at 504, and the timing counter in controller 106 times out the second cardioversion interval CINT-2 at 506. At the expiration of the second cardioversion interval at 506, controller 106 triggers the delivery of a cardioversion pulse at 508. Thereafter, controller 106 generates an interrupt which reawakens microprocessor 100, which in turn resets all event counters in controller 106 at 214 (FIG. 3) and clears the stored tachyarrhythmia intervals at 212, prior to returning to the brady pacing mode illustrated in FIG. 3.

Figure 7:
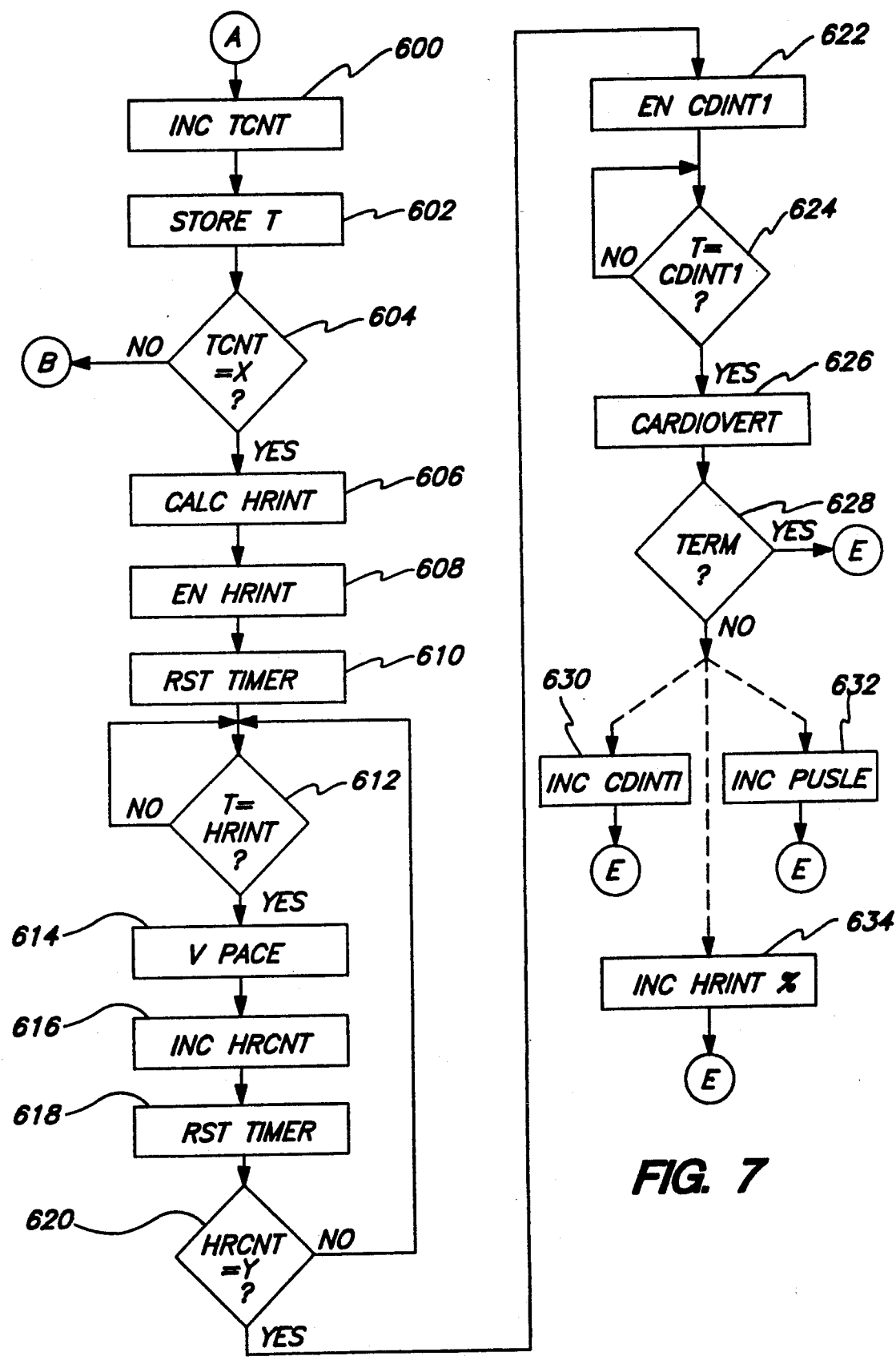
FIG. 7 is a functional flow chart illustrating the operation of a second embodiment of the device.

FIG. 7 illustrates an alternative method by which the implantable cardioverter/pacemaker verifies the existence of a tachyarrhythmia, initiates high rate pacing and delivers a cardioversion pulse. This method of cardioversion dispenses entirely with the capture detect function. In response detection of a tachyarrhythmic beat at 216 (FIG. 3), the value of TCNT is incremented at 600, and the duration of the detected tachyarrhythmic interval is stored at 602. The value of TCNT is compared with "X" at 604. Values chosen for X will generally fall in the range of 4 to 32 intervals meeting the tachyarrhythmia interval criteria. If the value of TCNT is less than X, the cardioverter/pacemaker returns to brady pacing via block 201. The timing counter is reset at 202. The controller continues to count out the refractory and escape intervals as illustrated in FIG. 3.

In the event that TCNT equals X, a new high rate interval is calculated at 606, as discussed in conjunction with block 306 (FIG. 4). The high rate pacing function is enabled at 608 and the timer is reset at 610. When the high 0 rate interval times out at 612, the controller 106 triggers generation of a pacing pulse at 614, increments the value of HRCNT at 616 and resets the timing counter at 618. The microprocessor 100 compares the stored HRCNT value with a predetermined number "Y" at 620, as discussed in conjunction with block 322 (FIG. 4). If this count has been reached a synchronous cardioversion timed off of the pacing pulse is initiated. If not, controller 106 continues to count out the next subsequent high rate pacing interval at 612.

The high rate pacing routine illustrated in FIG. 7 continues until the generation of the last available high rate pacing pulse, indicated by HRCNT equaling Y. In this event, synchronous cardioversion is enabled at 622. The value of Y may be 3 or greater. After determining at 620 that the high rate pacing routine has resulted in Y high rate pacing pulses delivered, controller 106 times out a cardioversion interval CDINT-1 at 624 and triggers the output stage 108 to generate a cardioversion pulse at the expiration of CDINT-1 at 626.

Block 628 represents a tachyarrhythmia termination detection function. Tachyarrhythmia termination is preferably identified by the detection of a sequence of a predetermined number of intervals between spontaneous R-waves which exceed a predetermined termination detection interval. The termination detection interval may be the same as or different from TINT. On failure to terminate at 628, the microprocessor is awakened from its sleep state, allowing it to calculate incremented values for one or more of the cardioversion interval at 630, the cardioversion pulse amplitude at 632 or the percentage of the detected tachyarrhythmia interval used to calculate the overdrive pacing interval at 634. Incrementation of the CDINT interval or the percentage discussed above may be positive or negative. Pulse amplitude incrementation should always be positive.

In the event that the cardioversion pulses delivered do not terminate the tachyarrhythmia, as indicated by a failure to detect termination of the tachyarrhythmia, the cardioversion therapy may be repeated using the incremented values discussed above. It is anticipated that the amplitude of the cardioversion pulse may in some cases increase from the amplitude normally necessary to convert a tachyarrhythmia to an amplitude more traditionally thought of as a defibrillation pulse. Alternatively, the present invention may be practiced in the context of a staged therapy device, such that in the event that the detected tachyarrhythmia rate exceeds a second, fibrillation detection rate, synchronized or unsynchronized defibrillation pulses may be generated using the same methodology as illustrated, or using other methods known to the prior art. Alternatively, the present invention could be practiced in the context of an implantable defibrillator which provides back-up bradycardia pacing, in which case the cardioversion pulses would all be of the amplitude normally required to cause defibrillation of the heart, and the high heart rate detection interval (TINT) would correspond to a heart rate normally associated with fibrillation. As such, it is believed that the present application is extremely flexible and may be embodied in several alternative types of devices. The above disclosure should therefore be considered exemplary, rather than limiting with regard to the following claims.

In conjunction with the above specification, I claim:
1. A cardioverter/pacemaker, comprising:
   means for detecting the occurrence of a tachyarrhythmia in a chamber of the heart;
   means responsive to said detecting means for measuring the rate of the detected tachyarrhythmia;
   means responsive to said detecting and measuring means for generating a series of a first predetermined number of pacing pulses, for application to said chamber of the heart, at a rate higher than the rate of the tachyarrhythmia detected by said detecting and measuring means; and
   cardioverting means for generating a cardioversion pulse a first predetermined time interval following the last of said first series of pacing pulses.
2. A cardioverter/pacemaker according to claim 1 further comprising means for determining whether said pacing pulses have been successful in capturing the heart.

3. A cardioverter/pacemaker according to claim 2 wherein in response to said determining means failing to determine the capture of the heart by at least a second number of sequential cardiac pacing pulses prior to said pulse generator means generating said first predetermined number of pacing pulses, said cardioverting means delivers a cardioversion pulse synchronized from a subsequent detected depolarization of said chamber of said heart.

4. A cardioverter/pacemaker according to claim 1 further comprising means for determining whether said cardioversion pulse successfully terminated said tachyarrhythmia and wherein said pulse generating means comprises means for delivering a second series of pacing pulses and for delivering a second cardioversion pulse a second predetermined interval following the last of said second series of pacing pulses.

5. A cardioverter/pacemaker according to claim 4 wherein said second interval differs from said first interval.

6. A cardioverter/pacemaker according to claim 4 further comprising means for increasing the energy of said cardioverting pulse following said second series of pacing pulses as compared to the energy level of said cardioversion pulse following said first series of pacing pulses.

7. A cardioverter/pacemaker according to claim 1 wherein said pulse generating means determines the intervals separating said first series of pacing pulses as a first percentage of the intervals separating the depolarizations of said detected tachyarrhythmia.

8. A cardioverter/pacemaker according to claim 4 wherein said pulse generating means determines the intervals separating said second series of pacing pulses as a second predetermined percentage of the intervals separating the depolarizations of said detected tachyarrhythmia differing from said first percentage.

9. A cardioverter/pacemaker, comprising:
means for detecting the occurrence of a tachyarrhythmia in a chamber of the heart;
means responsive to said detecting means for measuring the rate of the detected tachyarrhythmia;
means responsive to said detecting and measuring means for generating a series of pacing pulses, for application to said chamber of the heart, at a rate higher than the rate of the tachyarrhythmia detected by said detecting and measuring means;
means for determining whether said pacing pulses are successful in a capturing of said chamber of the heart; and
cardioverting means responsive to said determining means for generating a cardioversion pulse a predetermined time following one of said pacing pulses, when said determining means indicates that said pacing pulses have been successful in capturing said chamber of the heart.

10. A cardioverter/pacemaker according to claim 9 wherein said cardioversion means is responsive to said detect means for triggering the delivery of a cardioversion pulse synchronized to a subsequent natural contraction of said chamber of the heart, when said determining means indicates a failure of said pacing pulses to reliably capture the heart.

11. A cardioverter/pacemaker according to claim 9 or claim 10 wherein said determining means determines whether a sequential series of at least a predetermined number of said pacing pulses has been successful in capturing the heart.

12. A cardioverter/pacemaker according to claim 11 wherein said means for generating said series of pacing pulses generates a series of only up to a second predetermined number of sequential pacing pulses and wherein in response to said determining means failing to determine the capture of the heart by said first number of sequential cardiac pacing pulses prior to said pulse generator means generating said second predetermined number of pacing pulses, said cardioverting means delivers a cardioversion pulse synchronized from a subsequent detected contraction of said chamber of said heart.

13. A cardioverter/pacemaker according to claim 11 Wherein said means for generating said series of said pacing pulses generates a series of only up to a second predetermined number of pacing pulses, and wherein said cardioverting means is responsive to the occurrence of a first predetermined number of sequential pacing pulses successfully capturing the heart prior to the generation of said second number of pacing pulses by said pulse generator means, for triggering a cardioversion pulse a predetermined period following delivery of the final one of said pacing pulses.

14. A cardioverter/pacemaker, comprising:
means for detecting an occurrence of a tachyarrhythmia in a chamber of the heart;
means responsive to said detecting means for measuring the rate of detected tachyarrhythmia;
means responsive to a detection of an occurrence of a tachyarrhythmia for generating a series of pacing pulses for application to said chamber of the heart to trigger depolarizations of said chamber of the heart at a rate higher than the rate of the said tachyarrhythmia; and
means responsive to said detection of said occurrence of said tachyarrhythmia comprising means for generating a cardioversion pulse synchronized to the depolarization triggered by the last of said series of pacing pulses.

15. A cardioverter/pacemaker according to claim 14 wherein said cardioversion pulse generating means comprises means for triggering the generation of said cardioversion pulse a first predetermined time interval following said last of said series of pacing pulses.

16. A cardioverter/pacemaker according to claim 15 wherein said cardioversion pulse generating means further comprises means for determining whether said pacing pulses have been successful in capturing the heart and for triggering said generation of said cardioversion pulse said first predetermined time interval following said last of said series of pacing pulses only if said pacing pulses have been successful in capturing the heart.

17. A cardiovertor/pacemaker according to claim 16 further comprising means for defining a first predetermined number of pacing pulses and wherein said means for generating a series of pacing pulses comprises means for generating a series of up to said first predetermined number of pacing pulses.

18. A cardioverter/pacemaker according to claim 17 further comprising means for defining a second predetermined number of pacing pulses and wherein in response to said determining means determining the capture of the heart by at least said second predetermined number of sequential cardiac pacing pulses prior to said pacing pulse generating means generating said first predetermined number of pacing pulses, said pacing pulse generating means terminates delivery of said pacing pulses and said cardioverting means delivers a cardioversion pulse synchronized to the depolarization triggered by the last of said series of pacing pulses.

19. A cardioverter/pacemaker according to claim 17 or claim 18 further comprising means for defining a second predetermined number of pacing pulses, wherein said cardioversion pulse generating means further comprises means for generating cardioversion pulses synchronized to natural depolarizations and wherein in response to said determining means failing to determine the capture of the heart by at least said second predetermined number of sequential cardiac pacing pulses prior to said pacing pulse generating means generating said first predetermined number of pacing pulses, said cardioversion pulse generating means generates a cardioversion pulse synchronized to a subsequent detected natural depolarization of said chamber of said heart.

20. A cardioverter/pacemaker according to claim 19 wherein said cardioversion pulse generating means comprises means for generating a cardioversion pulse a second predetermined time interval following said subsequent detected natural depolarization of said chamber of said heart.

21. A cardioverter/pacemaker according to claim 20 wherein said second predetermined time interval differs from said first predetermined time interval.

22. A cardioverter/pacemaker, comprising:
means for detecting an occurrence of a series of depolarizations of said chamber of the heart indicative of tachyarrhythmia;
means responsive to said detecting means for measuring the rate of said series of depolarizations;
means for generating a cardioversion pulse in response to the detection of said series of depolarizations, comprising means for generating a series of pacing pulses following said series of depolarizations for application to said chamber of the heart to trigger depolarizations of said chamber of the heart at a rate higher than the rate of said series of depolarizations and for generating a cardioversion pulse synchronized to the last of said series of pacing pulses.

23. A cardioverter/pacemaker according to claim 22 wherein said cardioversion pulse generating means comprises means for triggering the generation of said cardioversion pulse a first predetermined time interval following said last of said series of pacing pulses.

24. A cardioverter/pacemaker according to claim 23 wherein said cardiovertor pulse generating means further comprises means for determining whether said series of pacing pulses has been successful in capturing the heart and for triggering said generation of said cardioversion pulse said first predetermined time interval following said last of said series of pacing pulses only if said pacing pulses have been successful in capturing the heart.

25. A cardioverter/pacemaker, comprising:
means for detecting an occurrence of a series of depolarizations of said chamber of the heart indicative of tachyarrhythmia;
means responsive to said detecting means for measuring the rate of said series of depolarizations;
means for generating both a series of pacing pulses for application to said chamber of the heart to trigger depolarizations of said chamber of the heart at a rate higher than the rate of said series of depolarizations and a cardioversion pulse a predetermined time interval after the last of said series of pacing pulses, following said detected series of depolarizations and in response only to said detected series of depolarizations.

26. A cardioverter/pacemaker, comprising:
means for detecting an occurrence of series of depolarizations of said chamber of the heart indicative of tachyarrhythmia and for providing an indication thereof for each said series of depolarizations;
means responsive to said detecting means for measuring the rate of said series of depolarizations;
means for generating both a series of pacing pulses for application to said chamber of the heart to trigger depolarizations of said chamber of the heart at a rate higher than the rate of said series of depolarizations and a cardioversion pulse a predetermined time interval after the last of said series of pacing pulses in response to a single one of said indications of an occurrence of a series of depolarizations of said chamber of the heart indicative of tachyarrhythmia.

* * * * *

UNITED STATES PATENT AND TRADEMARK OFFICE
CERTIFICATE OF CORRECTION

PATENT NO. : 5,193,536
DATED : March 16, 1993
INVENTOR(S) : Rahul Mehra

It is certified that error appears in the above-indentified patent and that said Letters Patent is hereby corrected as shown below:

Col. 2, line 19, "tachyarrh" should be --tachyarrhythmia--.

Col. 2, lines 20, --level of energy-- should be inserted after "reduction in the".

Col. 4, line 68, --and paced ventricular contractions are provided to the controller 106 via bus 128. Controller 106 passes data indicative of the occurrence of such ventricular contractions-- should be inserted after "ventricular contractions".

Col. 7, line 33, "22" should be --202--.

Col. 9, line 52, "high 0 rate" should be --high rate--.

Signed and Sealed this

Twenty-seventh Day of September, 1994

Attest:

BRUCE LEHMAN

*Attesting Officer*  *Commissioner of Patents and Trademarks*